United States Patent
Lyons et al.

(10) Patent No.: US 6,331,317 B1
(45) Date of Patent: Dec. 18, 2001

(54) APPARATUS AND METHOD FOR PREPARING MICROPARTICLES

(75) Inventors: Shawn L. Lyons, Cincinnati; Steven G. Wright, Madeira, both of OH (US)

(73) Assignee: Alkermes Controlled Therapeutics II Inc., Cambridge, MA (US)

( * ) Notice: Subject to any disclaimer, the term of this patent is extended or adjusted under 35 U.S.C. 154(b) by 0 days.

(21) Appl. No.: 09/438,659

(22) Filed: Nov. 12, 1999

(51) Int. Cl.[7] .............................. A61K 9/50; B01J 13/02
(52) U.S. Cl. .................. 424/489; 424/1.29; 424/490; 424/497; 424/501; 264/4.1; 264/4.33; 264/4.6; 428/402.21; 427/213.3; 427/213.36
(58) Field of Search ................... 424/1.29, 489, 424/490, 497, 501; 264/4.1, 4.33, 4.6; 428/402.21; 427/213.3, 213.36

(56) References Cited

U.S. PATENT DOCUMENTS

| | | |
|---|---|---|
| 3,523,906 | 8/1970 | Vrancken et al. . |
| 3,691,090 | 9/1972 | Kitajima et al. . |
| 3,737,337 | 6/1973 | Schnoring et al. . |
| 3,773,919 | 11/1973 | Boswell et al. . |
| 3,891,570 | 6/1975 | Fukushima et al. . |
| 3,960,757 | 6/1976 | Morishita et al. . |
| 4,221,862 | 9/1980 | Naito et al. . |
| 4,384,975 | 5/1983 | Fong . |
| 4,389,330 | 6/1983 | Tice et al. . |
| 4,530,840 | 7/1985 | Tice et al. . |
| 4,940,588 | 7/1990 | Sparks et al. . |
| 5,066,436 | 11/1991 | Komen et al. . |
| 5,407,609 | 4/1995 | Tice et al. . |
| 5,478,564 | 12/1995 | Wantier et al. . |
| 5,541,172 | 7/1996 | Labric et al. . |
| 5,650,173 | 7/1997 | Ramstack et al. . |
| 5,654,008 | 8/1997 | Herbert et al. . |
| 5,656,299 | 8/1997 | Kino et al. . |
| 5,688,801 | 11/1997 | Mesens et al. . |
| 5,770,231 | 6/1998 | Mesens et al. . |
| 5,792,477 | 8/1998 | Rickey et al. . |
| 5,871,778 | 2/1999 | Kino et al. . |
| 5,916,598 | 6/1999 | Rickey et al. . |
| 5,945,126 | 8/1999 | Thanoo et al. ................. 424/489 |
| 5,965,168 | 10/1999 | Mesens et al. . |

FOREIGN PATENT DOCUMENTS

| | | |
|---|---|---|
| 0 486 959 A1 | 5/1992 | (EP) . |
| WO 89/03678 | 5/1989 | (WO) . |
| WO 90/13361 | 11/1990 | (WO) . |
| WO 94/10982 | 5/1994 | (WO) . |
| WO 95/13799 | 5/1995 | (WO) . |
| WO 97/41837 | 11/1997 | (WO) . |
| WO 99/12549 | 3/1999 | (WO) . |

OTHER PUBLICATIONS

B. Conti et al., "Use of polylactic acid for the preparation of microparticulate drug delivery systems," J. Microencapsulation 1992, vol. 9, No. 2, pp. 153–166, XP 000259942.

Y.F. Maa et al., "Liquid–liquid emulsification by static mixers for use in microencapsulation," J. Microencapsulation, 1996, vol. 13, No. 4, pp. 419–433, XP 000589904.

Koch Engineering Co., Inc., Static Mixing Technology advertisement, pp. 1–15, (1991).

(List continued on next page.)

Primary Examiner—Samuel A. Acquah
(74) Attorney, Agent, or Firm—Andrea G. Reister; Covington & Burling

(57) ABSTRACT

Apparatus and method for preparing microparticles. An emulsion is formed by combining two phases in a static mixing assembly. The static mixing assembly preferably includes a preblending static mixer and a manifold. The emulsion flows out of the static mixing assembly into a quench liquid whereby droplets of the emulsion form microparticles. The residence time of the emulsion in the static mixing assembly is controlled to obtain a predetermined particle size distribution of the resulting microparticles.

44 Claims, 7 Drawing Sheets

OTHER PUBLICATIONS

Baker, J.R., "Motionless Mixers Stir Up New Uses," *Chemical Engineering Progress,* pp. 32–38 (Jun. 1991).

Mutsakis, M., et al., "Advances in Static Mixing Technology," *Chemical Engineering Progress,* pp. 42–48 (Jul. 1986).

Bodmeier, R., et al., International Journal of Pharmaceutics, 43:179–186 (1988).

Beck, L.R., et al., Biology of Reproduction, 28:186–195 (Feb. 1983).

Toyomi Sato et al., Pharmaceutical Research, 5:21–30 (1988).

Wen–I Li et al., Journal of Controlled Release, 37:199–214 (Dec. 1995).

H.V. Maulding et al., Journal of Controlled Release, 3;103–117 (Mar. 1986).

Hongkee Sah et al., Pharmaceutical Research, 13:360–367 (Mar. 1996).

R. Jalil et al., Journal of Microencapsulation, vol. 7, No. 3, Jul.–Sep. 1990, pp. 297–319.

APPARATUS AND METHOD FOR PREPARING MICROPARTICLES

CROSS-REFERENCE TO RELATED APPLICATIONS

This application is related to co-pending application Ser. No. 09/223,276 entitled "Apparatus and Method for Preparing Microparticles Using In-Line Solvent Extraction", filed on even date herewith, the entirety of which is incorporated herein by reference.

BACKGROUND OF THE INVENTION

1. Field of the Invention

The present invention relates to preparation of microparticles. More particularly, the present invention relates to a method and an apparatus for preparing microparticles having a more controlled and symmetrical particle size distribution.

2. Related Art

A variety of methods is known by which compounds can be encapsulated in the form of microparticles. It is particularly advantageous to encapsulate a biologically active or pharmaceutically active agent within a biocompatible, biodegradable wall forming material (e.g., a polymer) to provide sustained or delayed release of drugs or other active agents. In these methods, the material to be encapsulated (drugs or other active agents) is generally dissolved, dispersed, or emulsified, using stirrers, agitators, or other dynamic mixing techniques, in a solvent containing the wall forming material. Solvent is then removed from the microparticles and thereafter the microparticle product is obtained.

Development of a microencapsulation process suitable for commercial scale production typically requires scaling up, by multiple factors, a laboratory scale process and/or a pilot scale process. The scaled-up process will almost always require larger piping and higher flow rates, particularly when the scale factor is very large or if it is desired or necessary to keep process transfer times similar to the smaller scale processes. Scale-up into new, larger equipment is often unpredictable and achieved in large measure through trial and error. However, the economic costs of large-scale trial and error experiments can be prohibitive.

One approach to aiding the scale-up process is to use a static mixer to form an emulsion, as disclosed in U.S. Pat. No. 5,654,008. In the method disclosed in U.S. Pat. No. 5,654,008, a first phase, comprising the active agent and the polymer, and a second phase are pumped through a static mixer into a quench liquid to form microparticles containing the active agent. The use of a static mixer to form the emulsion tends to make the scale-up more predictable and reliable than the scale-up of other dynamic-mixing processes for making microparticles. However, numerous trials and experiments are still required to completely and accurately scale-up, such as to commercial scale or by a factor of 20 or more, a process such as the one disclosed in U.S. Pat. No. 5,654,008.

For a commercial scale process, it is particularly important to control the distribution of the size of the microparticles to minimize yield losses. For example, microparticles, particularly controlled release microparticles containing an active agent or other type of substance to be released, can range in size of from about 25 $\mu$m to about 250 $\mu$m in diameter. For a particular commercial product, the useful or desired microparticle size range can be in the range of, for example, 25–150 $\mu$m. Even in an efficient commercial production process, some percentage of the microparticles produced will be larger than the upper size limit, and some percentage of the microparticles produced will be smaller than the lower size limit, resulting in yield losses. Typically, the more narrow or tighter the desired microparticle size range, the larger the yield losses that result. These yield losses could be avoided or minimized if a more narrow microparticle size distribution could be achieved. Narrowing the microparticle size distribution eliminates or significantly reduces the losses resulting from microparticles that fall outside of the desired microparticle size range.

Thus, there is a need in the art for an improved method and apparatus for preparing microparticles. There is a particular need in the art for an improved process that can control particle size distribution, and achieve a more narrow particle size distribution. There is a further need in the art for an improved process that can be more quickly, reliably, and accurately scaled-up from a laboratory or pilot scale to a commercial scale. The present invention, the description of which is fully set forth below, solves the need in the art for such improved methods and apparatus.

SUMMARY OF THE INVENTION

The present invention relates to an apparatus and method for preparing microparticles. In one aspect of the invention, a method of preparing microparticles is provided. The method comprises:

preparing a first phase, the first phase comprising an active agent and a polymer;

preparing a second phase;

preparing a quench liquid;

pumping the first phase and the second phase through a first static mixer to form an emulsion; and flowing the emulsion through a manifold that includes a plurality of static mixers into the quench liquid whereby droplets of the emulsion form microparticles.

In a further aspect of the present invention, another method for preparing microparticles is provided. The method comprises:

preparing a first phase, the first phase comprising an active agent and a polymer;

preparing a second phase;

preparing a quench liquid;

combining the first phase and the second phase in a first static mixer to form an emulsion, the emulsion forming an outflow of the first static mixer;

dividing the outflow of the first static mixer to form at least two flow streams;

flowing each of the at least two flow streams through a separate second static mixer; and combining the at least two flow streams with the quench liquid whereby droplets of the emulsion form microparticles.

In a further aspect of the present invention, a method for controlling particle size distribution of microparticles is provided. The method comprises:

preparing a first phase, the first phase comprising an active agent and a polymer;

preparing a second phase;

preparing a quench liquid;

pumping the first phase and the second phase through a static mixing assembly to form an emulsion;

flowing the emulsion into the quench liquid whereby droplets of the emulsion form microparticles; and adjusting a residence time of the emulsion in the static mixing assembly to obtain a predetermined particle size distribution of the resulting microparticles, wherein the residence time is equal to a length of the static mixing assembly divided by an average velocity of the emulsion through the static mixing assembly.

In yet a further aspect of the present invention, a microencapsulated active agent prepared by a method for preparing microparticles is provided. Such a method comprises:

preparing a first phase, the first phase comprising an active agent and a polymer;

preparing a second phase;

preparing a quench liquid;

pumping the first phase and the second phase through a first static mixer to form an emulsion; and flowing the emulsion through a manifold that includes a plurality of static mixers into the quench liquid whereby droplets of the emulsion form microparticles.

In yet a further aspect of the present invention, a microencapsulated active agent prepared by another method for preparing microparticles is provided. Such a method comprises:

preparing a first phase, the first phase comprising an active agent and a polymer;

preparing a second phase;

preparing a quench liquid;

combining the first phase and the second phase in a first static mixer to form an emulsion, the emulsion forming an outflow of the first static mixer;

dividing the outflow of the first static mixer to form at least two substantially identical flow streams;

flowing each of the at least two substantially identical flow streams through a separate second static mixer; and combining the least two substantially identical flow streams with the quench liquid whereby droplets of the emulsion form microparticles.

In still a further aspect of the present invention, a system for preparing microparticles is provided. The system includes a first and second pump, and a first static mixer in fluid communication with each of the pumps. One of the pumps is configured to pump an organic phase into the first static mixer. One of the pumps is configured to pump a continuous phase into the first static mixer. A manifold, comprising a plurality of static mixers, is in fluid communication with the first static mixer. An extraction vessel is in fluid communication with the manifold. The outflow of the first static mixer flows through the manifold into the extraction vessel. The plurality of static mixers in the manifold can be configured in parallel or in series.

Features and Advantages

It is a feature of the present invention that it can be used to prepare microparticles, including microparticles containing an active agent.

A significant advantage of the present invention is that it provides a method for controlling particle size distribution. By controlling particle size distribution, yield losses, resulting from microparticles that fall outside of a desired microparticle size range, can be substantially reduced or eliminated. This makes the present invention particularly useful for commercial products.

The present invention also advantageously allows for use of a more narrow or tighter target microparticle size range than in conventional processes. Narrowing the limit for the microparticle size range typically results in larger yield losses. These yield losses can be avoided or minimized by achieving a more narrow microparticle size distribution through the process of the present invention.

The present invention provides a method and apparatus that are particularly advantageous for scale-up. The parallel path manifold of the present invention allows for capacity increases from an established (single path) system without full-scale trial and error experiments in new and different equipment. The total flow rate can be increased from the single path system based upon the number of flow streams in the manifold.

BRIEF DESCRIPTION OF THE FIGURES

The present invention is described with reference to the accompanying drawings. In the drawings, like reference numbers indicate identical or functionally similar elements.

DETAILED DESCRIPTION OF THE PREFERRED EMBODIMENTS

Overview

Figure 1:
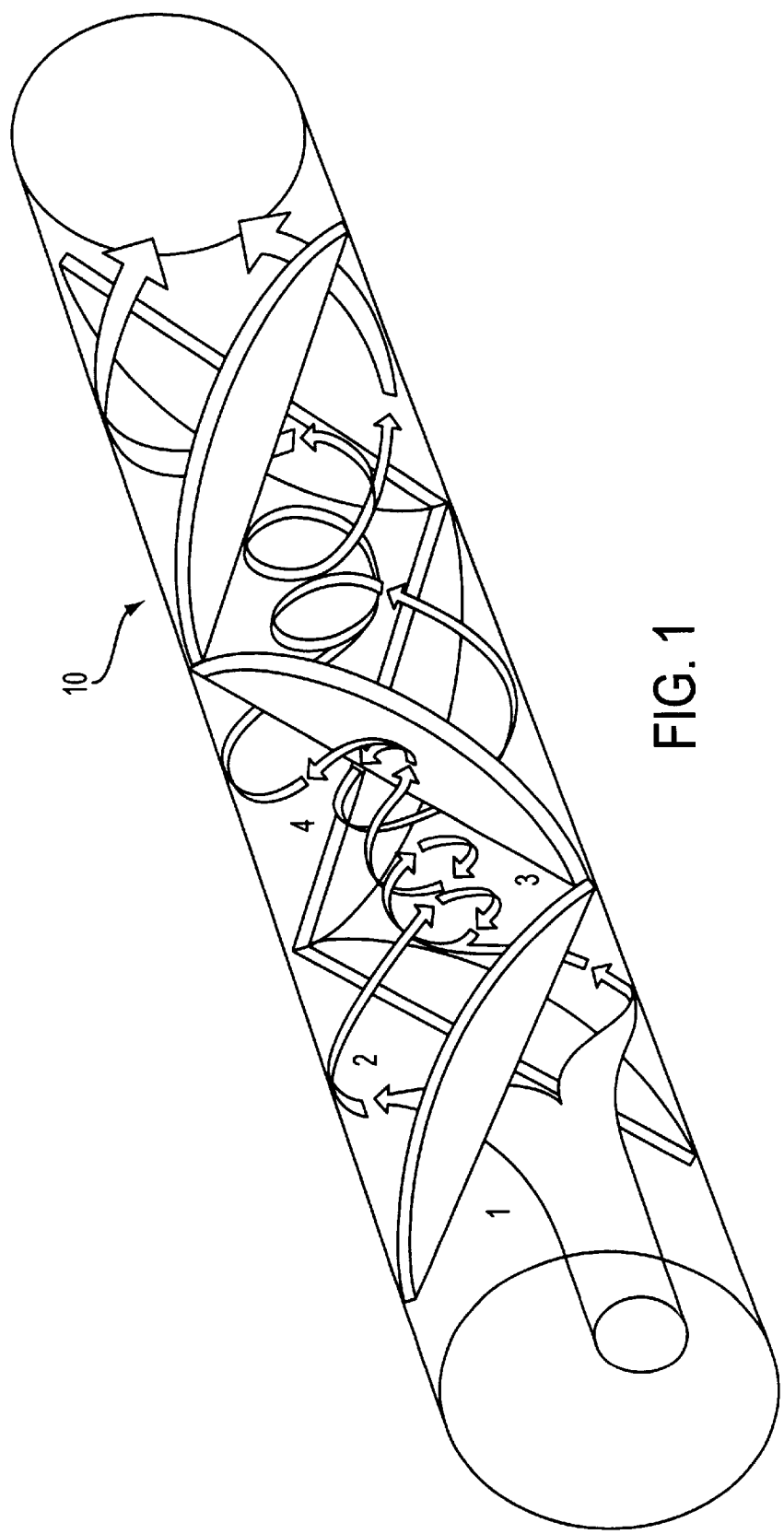
FIG. 1 illustrates flow through a static mixer.

The present invention provides an improved method and apparatus for preparing microparticles. Maximum yield within a desired microparticle size range is an important aspect of any process or method for preparing microparticles. The size of the resulting microparticles is primarily controlled during the emulsification step of the process of the present invention. As will be explained in more detail below, the emulsification step uses an in-line motionless or static mixer to create an emulsion from a first phase, comprising a polymer and a drug or other active agent, and a second phase, preferably an aqueous solution. The inventors of the present invention have unexpectedly found that the most dominant influential characteristic controlling the dispersity of microparticle size is the residence time of the emulsion in the static mixer before the emulsion is introduced to a quench or solvent-extraction liquid. Increased residence time in the emulsion-forming static mixer decreases polydispersity, and results in a more symmetrical particle size distribution.

The methods of the present invention use a static mixer to combine a first phase, comprising an active agent and a polymer, with a second phase to form an emulsion. The static mixer in which the first and second phases are combined to form the emulsion may be referred to herein as a "preblending static mixer". A process for forming an emulsion using a static mixer is described, for example, in U.S. Pat. No. 5,654,008, the entirety of which is incorporated herein by reference. The phase comprising the active agent and the polymer may be referred to herein as the "organic phase". The other phase may be referred to herein as the "continuous phase".

The emulsion flowing out of the preblending static mixer flows through a manifold containing a plurality of static mixers into a quench liquid whereby droplets of the emulsion form microparticles. Alternatively, the outflow of the preblending static mixer is divided to form at least two flow streams. Each of the flow streams then flows through another separate static mixer. The flow streams are recombined downstream, and combined with the quench liquid whereby droplets of the emulsion form microparticles.

In a particularly preferred embodiment, the diameter of the preblending static mixer is greater than the diameter of the static mixers in the manifold, i.e., greater than the diameter of the static mixers through which the divided flow streams flow. When using a static mixer to form an emulsion, a variety of factors determine emulsion droplet size. Emulsion droplet size determines the size of the resulting microparticles. These factors include the density and viscosity of the various solutions or phases to be mixed, volume ratio of the phases, interfacial tension between the phases, static mixer parameters (conduit diameter; length of mixing elements; number of mixing elements), and fluid velocity through the static mixer. The primary controlling variable is fluid velocity. Droplet size decreases as fluid velocity increases. Similarly, droplet size increases as fluid velocity (and pressure drop) decreases. Accordingly, the preblending static mixer is preferably larger in diameter than the static mixers in the manifold in order to handle the total flow from the feed streams (organic phase and continuous phase) at a lower velocity than the smaller diameter static mixers in the manifold.

In the present invention, a preblending static mixer is used to combine the organic phase and the aqueous phase to form the emulsion. In one embodiment, the emulsion is divided into a plurality of flow streams for flow through the manifold. The use of the preblending static mixer prior to the manifold is particularly advantageous because the organic phase and the aqueous phase are not immediately miscible or homogeneous, making the division of the combined flow stream problematic. For multiphase (e.g., oil/water) streams, the use of the manifold without the preblending static mixer could result in different compositions in each static mixer in the manifold. Because the combined organic and aqueous phases is not homogeneous, it would not divide evenly in conventional piping.

The manifold configuration of the present invention is particularly advantageous for scale-up. The parallel path manifold of the smaller diameter static mixers allows for capacity increases from an established (single path) system without full-scale trial and error experiments in new and different equipment. The total flow rate can be increased from the single path system based upon the number of flow streams in the manifold.

The present invention advantageously provides a method for controlling particle size distribution of microparticles. A first phase, comprising an active agent and a polymer, and a second phase are pumped through a static mixing assembly to form an emulsion. The emulsion flows into a quench liquid, whereby droplets of the emulsion form microparticles. By adjusting a residence time of the emulsion in the static mixing assembly, a predetermined particle size distribution of the resulting microparticles can be obtained. The residence time is equal to a length of the static mixing assembly divided by an average velocity of the emulsion through the static mixing assembly. The particle size distribution can be narrowed by increasing the residence time. The particle size distribution can be broadened by decreasing the residence time. The residence time is preferably adjusted by changing the length of the static mixing assembly.

To ensure clarity of the description that follows, the following definitions are provided. By "microparticles" or "microspheres" is meant solid particles that contain an active agent or other substance dispersed or dissolved within a polymer that serves as a matrix or binder of the particle. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per total weight of microparticle. For example, 10 wt. % active agent would mean 10 parts active agent by weight and 90 parts polymer by weight. Unless otherwise indicated to the contrary, percentages (%) reported herein are by weight. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

METHOD AND EXAMPLES

The following examples are provided to explain the invention, and to describe the materials and methods used in carrying out the invention. The examples are not intended to limit the invention in any manner.

Example 1

Static Mixer Tests

A test program was conducted using a variety of static mixers. A static or motionless mixer consists of a conduit or tube in which is received a number of static mixing elements. Static mixers provide uniform mixing in a relatively short length of conduit, and in a relatively short period of time. With static mixers, the fluid moves through the mixer, rather than some part of the mixer, such as a blade, moving through the fluid. Flow through one type of static mixer is illustrated in FIG. 1. A pump (not shown) introduces a stream of one or more fluids into a static mixer 10, as shown generally at 1. The stream is split and forced to opposite outside walls, as shown generally at 2. A vortex is created axial to the centerline of static mixer 10, as shown generally at 3. The vortex is sheared and the process recurs, but with the opposite rotation, as shown generally at 4. The clockwise/counterclockwise motion ensures a homogeneous product.

Figure 2:
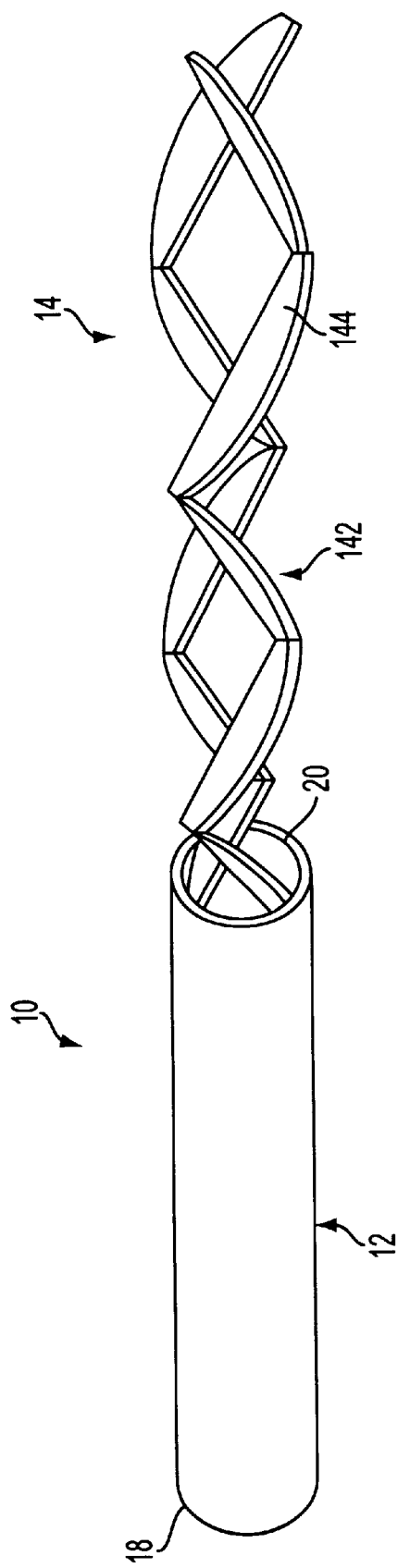
FIG. 2 shows a static mixer suitable for use with the present invention.

One example of a static mixer is shown in FIG. 2. Static mixer 10 includes a number of stationary or static mixing elements 14 arranged in a series within a conduit or pipe 12. The number of static mixing elements can range from 4 to 32 or more. Conduit 12 is circular in cross-section and open at opposite ends 18 and 20 for introducing and withdrawing fluids. Mixing element 14 comprises segments 142. Each segment 142 consists of a plurality of generally flat plates or vanes 144. The two substantially identical segments 142 are preferably axially staggered with respect to each other. A static mixer as shown in FIG. 2 is more fully described in U.S. Pat. No. 4,511,258, the entirety of which is incorporated herein by reference.

Figure 3A:
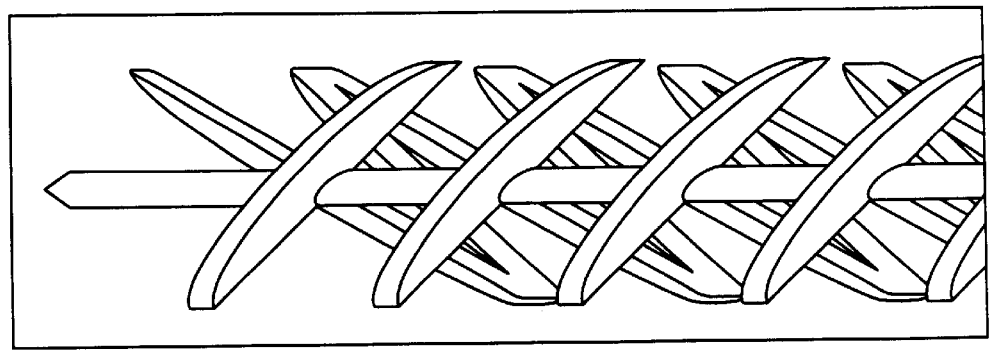
FIGS. 3A–3C show various types or designs of static mixing elements.
Figure 3B:
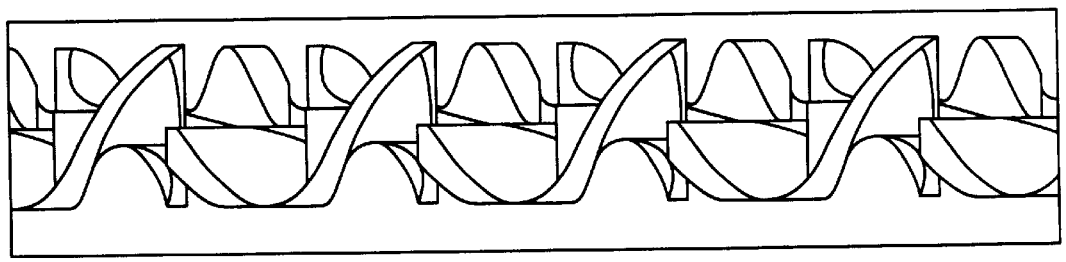
Figure 3C:
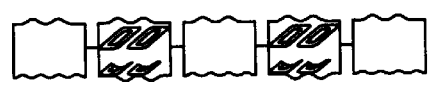

Each of the static mixers tested displayed characteristic differences in design, length, diameter, and number of elements per length. A key aspect to the design of a static mixer is the geometry of the static mixing elements. The eight static mixers tested used three different types of static mixing elements: scissors elements; helical elements; and layered elements. A scissors mixing element, shown in FIG. 3A, has two rows of baffles affixed perpendicular to each other, creating the impression of a pair of opened scissors. A helical mixing element, shown in FIG. 3B, uses a 180° helical plane with a 90° offset and alternating direction of sequential elements. A layered element, shown in FIG. 3C, uses corrugated sheets welded together to form open channels.

The characteristics of the eight static mixers tested are shown below in Table 1. The mixers ranged in size from 2½ inches in length with 5 mixing elements to 9¾ inches in length with 24 mixing elements. By arranging identical static mixers in series, the length and the number of mixing elements was increased; however, the number of mixing elements per unit length remained constant. The diameter of the static mixers tested ranged from ¼ inch to ½ inch.

TABLE 1

Characteristics of the Test Mixers

| Mixer # | Diameter | Length | # of Elements | Element Design | Material | Manufacturer |
|---|---|---|---|---|---|---|
| 1 | ¼" | 6" | 24 | Helical | Plastic | Cole Palmer |
| 2 | ¼" | 9¾" | 24 | Relical | Stainless Steel | TAH |
| 3 | ⅜" | 4¾" | 12 | Helical | Plastic | Cole Palmer |
| 4 | ⅜" | 9" | 12 | Helical | Stainless Steel | Kenics |
| 5 | ⅜" | 2½" | 5 | Layered | Stainless Steel | Koch |
| 6 | ½" | 5" | 12 | Helical | Plastic | TAH |
| 7 | ½" | 6" | 12 | Helical | Plastic | Cole Palmer |
| 8 | 5/16" | 2⅞" | 12 | Scissors | Plastic | Omega |

One-hundred gram batches of 40% theoretically loaded risperidone microparticles were used to test the static mixers. A 16.7% polymer solution was prepared by dissolving 60 grams of MEDISORB® 7525 DL polymer (Alkermes, Inc., Blue Ash, Ohio) in ethyl acetate. A 28.6% drug solution was prepared by dissolving 40 grams of risperidone base (Janssen Pharmaceutica, Beerse, Belgium) in benzyl alcohol. The organic phase was prepared by mixing the drug solution into the polymer solution. The continuous or aqueous phase was a 1% polyvinyl alcohol (PVA) solution containing 6.5% ethyl acetate. The temperature of the organic and aqueous phases was 25° C. The ratio of the aqueous phase to the organic phase was 5:1. The quench liquid or extraction solution was an aqueous solution containing 2.5% ethyl acetate at 25° C. The ratio of the volume of extraction solution to batch size was 0.25 liters/gram.

The 100-gram batches were produced by forming an oil-in-water emulsion, and then extracting the solvent from the emulsion droplet to form a hardened polymer/drug microparticle. Two calibrated micropumps fed the static mixer under test, one micropump for the organic phase and one micropump for the aqueous phase. The micropumps were calibrated by monitoring total volume pumped over a timed period prior to the batch being run. A "Y" connection upstream of the static mixer under test was used to introduce the organic phase into the aqueous phase.

The static mixer under test discharged the resulting emulsion directly into an agitated extraction solution. The emulsion remained in the extraction solution for fifteen minutes to harden into microparticles. A sample of the resulting microparticles was tested using a Coulter LS230 Small Module particle size analyzer to determine particle size distribution. The flow rates were adjusted to target a mass median diameter of between about 30 μm and 90 μm. The experimental results for the eight static mixers tested is shown below in Table 2.

TABLE 2

Summary of Experimental Results

| | | Process Conditions | | | | Cal. | | Particle Data | | | | | | |
|---|---|---|---|---|---|---|---|---|---|---|---|---|---|---|
| Mixer Number | Geometry | Diameter (in) | Elements (#) | Length (in) | Total Flow (ml/min) | Cal. Velocity (cm/min) | Residence Time (sec) | Median (um) | @ 84% (um) | @ 16% (um) | $CoV_m$ | Mean (um) | $CoV_x$ | Skewness |
| 1 | Helical | 0.250 | 24 | 6.00 | 971 | 3068 | 0.298 | 24.60 | 43.88 | 6.07 | 1.54 | 25.45 | 0.666 | 0.259 |
| 1 | Helical | 0.250 | 24 | 6.00 | 464 | 1467 | 0.623 | 54.56 | 92.01 | 18.83 | 1.34 | 55.85 | 0.606 | 0.260 |
| 1 | Helical | 0.250 | 24 | 6.00 | 329 | 1039 | 0.880 | 87.76 | 159.10 | 33.30 | 1.43 | 97.33 | 0.667 | 0.846 |
| 2 | Helical | 0.250 | 24 | 9.75 | 960 | 3033 | 0.490 | 57.28 | 120.80 | 16.65 | 1.82 | 67.37 | 0.748 | 0.751 |
| 3 | Helical | 0.375 | 12 | 4.75 | 1140 | 1600 | 0.452 | 43.20 | 88.64 | 13.59 | 1.74 | 50.01 | 0.723 | 0.737 |
| 3 | Helical | 0.375 | 12 | 4.75 | 1213 | 1703 | 0.425 | 47.93 | 89.66 | 18.40 | 1.49 | 53.2 | 0.627 | 0.590 |
| 3 | Helical | 0.375 | 12 | 4.75 | 1215 | 1706 | 0.424 | 47.13 | 90.58 | 15.14 | 1.60 | 52.11 | 0.677 | 0.532 |

TABLE 2-continued

Summary of Experimental Results

| | | Process Conditions | | | | | Particle Data | | | | | | |
|---|---|---|---|---|---|---|---|---|---|---|---|---|---|
| Mixer Number | Geometry | Diameter (in) | Elements (#) | Length (in) | Total Flow (ml/min) | Cal. Velocity (cm/min) | Cal. Residence Time (sec) | Median (um) | @ 84% (um) | @ 16% (um) | $CoV_m$ | Mean (um) | $CoV_x$ | Skewness |
| 3 | Helical | 0.375 | 60 | 23.50 | 1133 | 1591 | 2.251 | 53.25 | 85.31 | 18.70 | 1.25 | 52.8 | 0.577 | 0.127 |
| 3 | Helical | 0.375 | 144 | 57.00 | 1036 | 1455 | 5.971 | 54.11 | 90.86 | 19.96 | 1.31 | 55.71 | 0.593 | 0.326 |
| 4 | Helical | 0.375 | 12 | 9.00 | 2792 | 3920 | 0.350 | 70.62 | 150.60 | 24.41 | 1.79 | 85.34 | 0.745 | 0.911 |
| 4 | Helical | 0.375 | 12 | 9.00 | 3527 | 4952 | 0.277 | 53.28 | 105.90 | 21.45 | 1.59 | 61.93 | 0.654 | 0.754 |
| 4 | Helical | 0.375 | 12 | 9.00 | 3703 | 5199 | 0.264 | 45.40 | 98.83 | 15.00 | 1.85 | 55.7 | 0.781 | 1.075 |
| 4 | Helical | 0.375 | 12 | 9.00 | 3487 | 4896 | 0.280 | 52.11 | 113.70 | 17.34 | 1.85 | 64.37 | 0.789 | 1.150 |
| 4 | Helical | 0.375 | 36 | 27.00 | 2888 | 4055 | 1.015 | 81.66 | 131.20 | 31.68 | 1.22 | 82.36 | 0.556 | 0.226 |
| 5 | Layered | 0.375 | 5 | 2.50 | 1166 | 1637 | 0.233 | 109.60 | 248.20 | 29.14 | 2.00 | 133.5 | 0.769 | 0.682 |
| 5 | Layered | 0.375 | 5 | 2.50 | 2423 | 3402 | 0.112 | 29.37 | 58.21 | 6.71 | 1.75 | 32.89 | 0.743 | 0.730 |
| 6 | Helical | 0.500 | 12 | 5.00 | 2764 | 2183 | 0.349 | 42.25 | 82.85 | 13.19 | 1.65 | 47.27 | 0.693 | 0.577 |
| 7 | Helical | 0.500 | 12 | 6.00 | 3929 | 3103 | 0.295 | 21.51 | 43.89 | 4.75 | 1.82 | 24.22 | 0.731 | 0.546 |
| 7 | Helical | 0.500 | 12 | 6.00 | 3507 | 2770 | 0.330 | 29.67 | 57.92 | 7.59 | 1.70 | 32.68 | 0.705 | 0.499 |
| 7 | Helical | 0.500 | 12 | 6.00 | 2684 | 2120 | 0.431 | 40.03 | 71.89 | 12.50 | 1.48 | 42.05 | 0.638 | 0.283 |
| 7 | Helical | 0.500 | 36 | 18.00 | 2779 | 2195 | 1.250 | 48.37 | 83.19 | 15.68 | 1.40 | 49.52 | 0.614 | 0.189 |
| 8 | Scissors | 0.313 | 12 | 2.88 | 909 | 1838 | 0.238 | 23.66 | 48.68 | 4.88 | 1.85 | 26.75 | 0.742 | 0.579 |
| 8 | Scissors | 0.313 | 12 | 2.88 | 620 | 1254 | 0.350 | 58.77 | 104.90 | 20.11 | 1.44 | 62.83 | 0.650 | 0.574 |

The average emulsion velocity and residence time through a static mixer can be calculated from the flow rate into the static mixer and the length and diameter of the static mixer as follows:

(1) Average Velocity=flow rate/cross-sectional area of empty static mixer
(2) Residence Time=length of static mixer/Average Velocity To characterize the particle size distribution, these parameters were measured: median, coefficient of variation of the median and skewness. The coefficient of variation of the median ($CoV_m$) was used to characterize the span of the distribution.

$$CoV_m = \frac{(\text{diameter of } \mu\theta \text{ at } 84\% - \text{diameter of } \mu\theta \text{ at } 16\%)}{MMD} \quad (3)$$

As the $CoV_m$ approached zero, the distribution became more monodispered. The symmetry of the distribution was determined using the skewness coefficient. The Coulter analyzer's method of determining skewness is as follows:

$$Skewness = \frac{\sum [n_c(x_c - x_a)^3)}{SD^3 \sum n_c}$$

$n_c$ = # of particles in $c$'th channel
$x_c$ = mean volume in the $c$'th channel
$x_a$ = arithmetic mean of the distribution
$SD$ = standard deviation of the distribution As the distribution became more symmetrical, the skewness approached zero. For right-skewed distributions (the particle size of the mode is less than the mean) the coefficient is positive; for left-skewed, the coefficient is negative.

Figure 4:
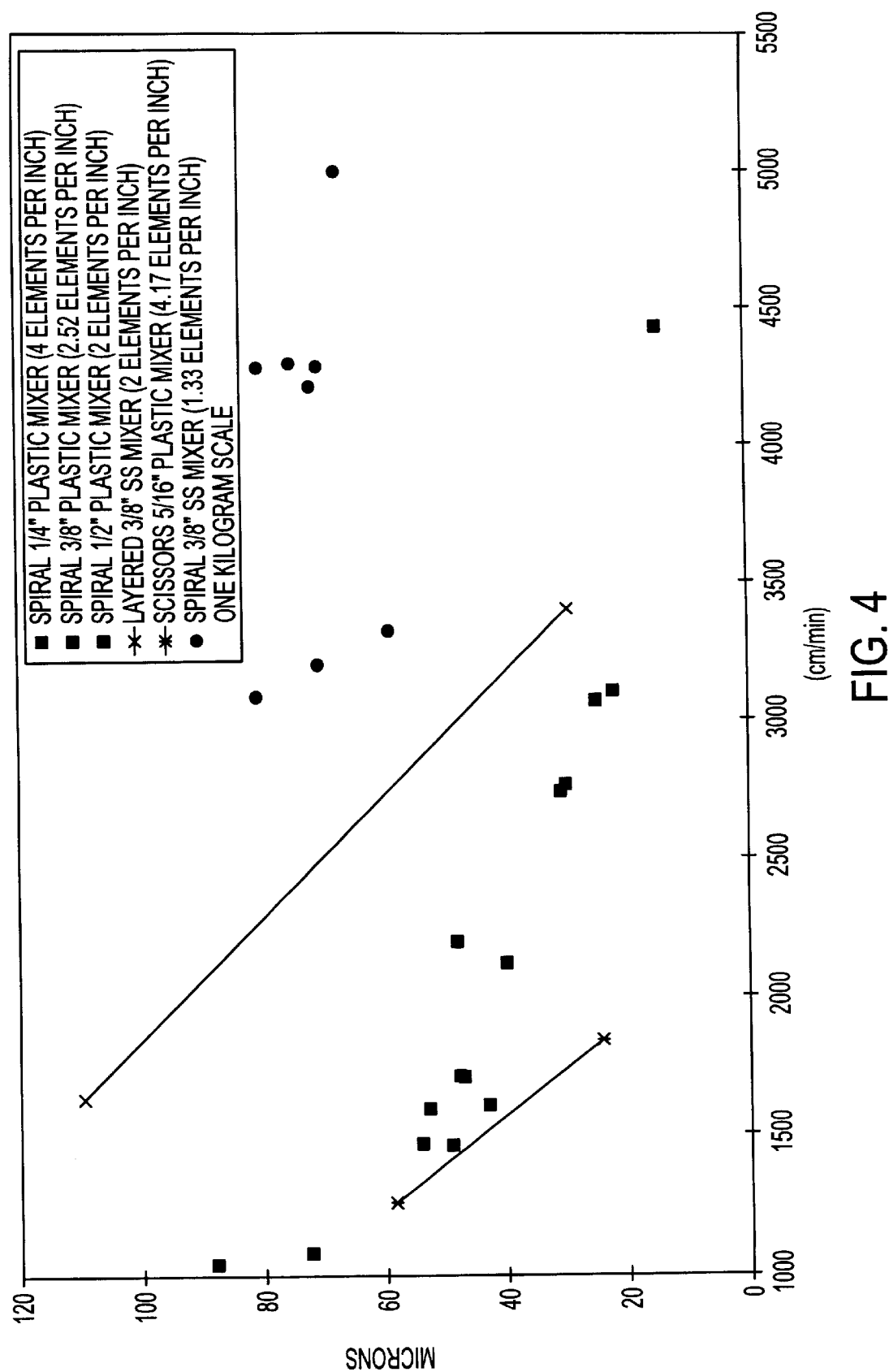
FIG. 4 depicts a graph of mass median diameter (microns) of microparticle size distribution as a function of average emulsion velocity (cm/min)

FIG. 4 shows the effect of the average emulsion velocity (cm/min) on the mass median diameter (MMD, microns) of the size distribution for the various static mixers under test. As shown in FIG. 4, the MMD data for the plastic helical design mixer indicate a consistent well behaved inverse relationship between MMD and average velocity, independent of mixer diameter, length, and number of elements per length. The layered stainless steel (SS) mixer and the plastic scissors mixer also demonstrated an inverse relationship between MMD and average velocity. FIG. 4 shows MMD data for a helical stainless steel (SS) mixer used to produce microparticles at the one kilogram scale, in a manner analogous to that described above for the 100 gram scale. The inverse relationship between MMD and average velocity was not readily apparent from the experimental data obtained with the stainless steel helical mixer at the one kilogram scale. Notably, this static mixer had the fewest elements per length (1.33 elements per inch) of all the static mixers tested.

Figure 5:
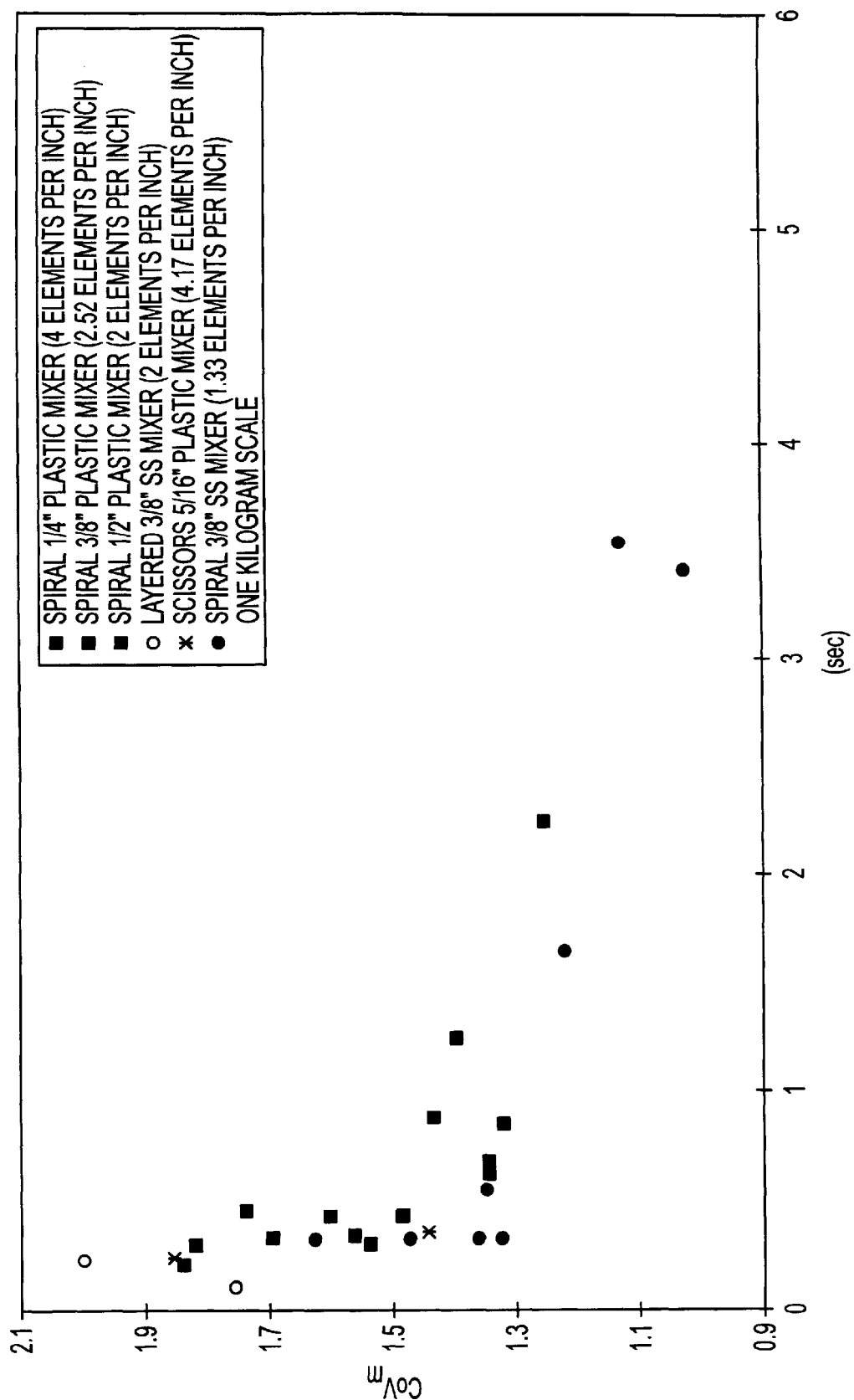
FIG. 5 depicts a graph of width of microparticle size distribution, as expressed by $CoV_m$, for various static mixers as a function of emulsion residence time (sec) in the static mixer.

FIG. 5 shows the effect of emulsion residence time (sec) in the static mixer on the width of the microparticle size distribution ($CoV_m$) using the various static mixers under test. An increase in residence time of the emulsion flowing through the static mixer causes a decrease in the width of the microparticle size distribution, until a minimum is reached. The data at extremely low residence times (less than one second) have high variability, but consistently show an increase in the width of the particle size distribution as the residence time decreases below one second.

Figure 6:
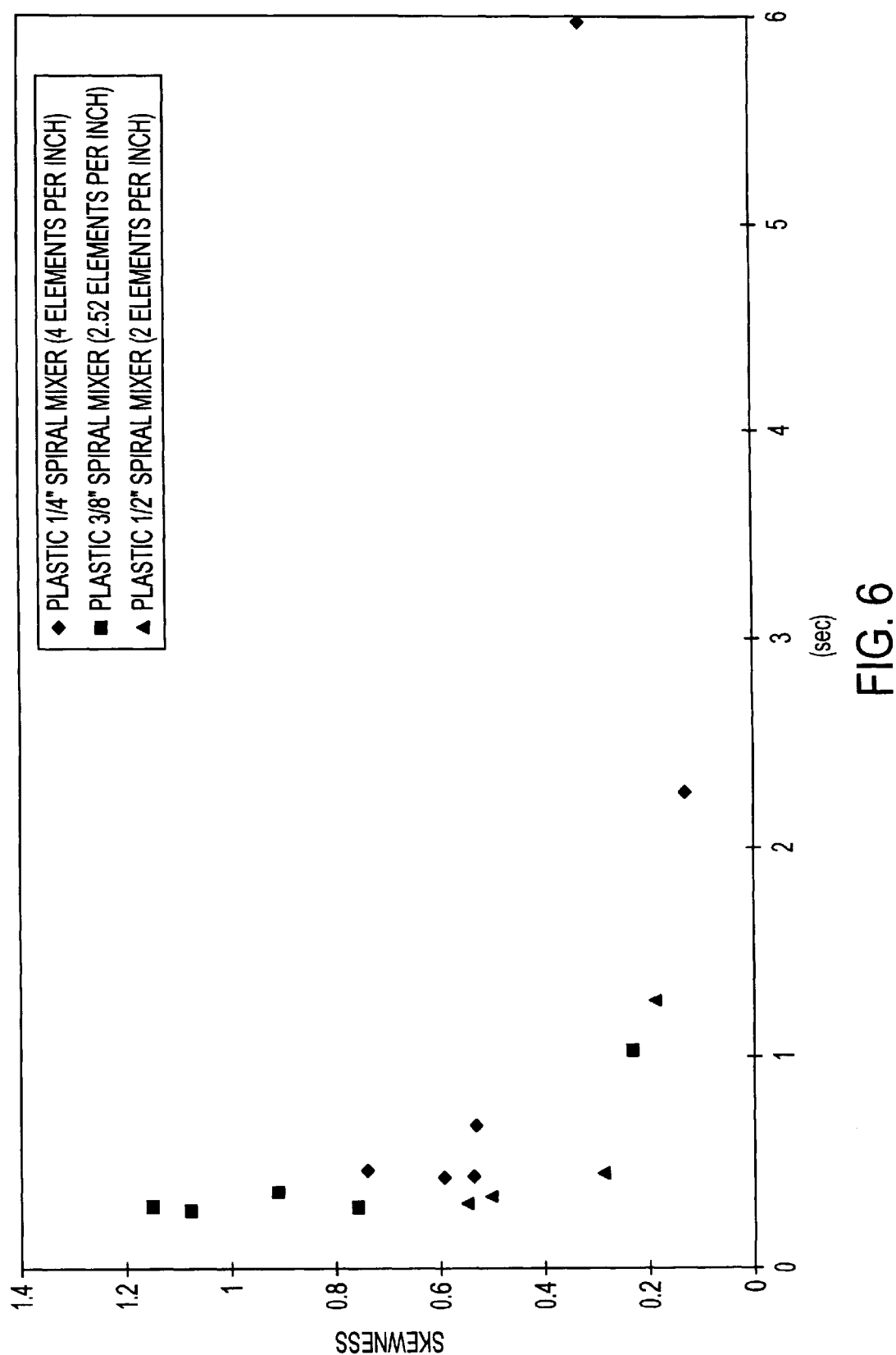
FIG. 6 depicts a graph of skewness of microparticle size distribution for various static mixers as a function of emulsion residence time (sec) in the static mixer.

FIG. 6 shows the effect of emulsion residence time (sec) in the static mixer on the skewness of the microparticle size distribution. As shown in FIG. 6, as residence time increased, the skewness of the microparticle size distribution decreased. All of the distributions were right-skewed.

Experiments were also performed at the one kilogram scale, in a manner analogous to that described above for the 100 gram scale. However, for the one kilogram experiments, the number of static mixers was varied, using one, two, four, and eight static mixers arranged in series. The results of the one kilogram scale experiments are shown below in Table 3.

TABLE 3

| Batch # | # of Mixers | Flow Rate (ml/min) | Cal. Velocity (cm/min) | Cal. Residence Time (sec) | Median (um) | @ 84% (um) | @ 16% (um) | CoV$_m$ | @ 25 um % | @ 125 um % | @ 150 um % | 25–125 yield* % | 25–150 yield* % |
|---|---|---|---|---|---|---|---|---|---|---|---|---|---|
| 1kg-0210-7 | 1 | 3060 | 4297 | 0.319 | 74.85 | 135.1 | 24.98 | 1.47 | 17.94 | 78.31 | 88.85 | 70.37 | 70.91 |
| -0218-7 | 1 | 3050 | 4283 | 0.320 | 79.95 | 135.4 | 29.85 | 1.32 | N/R | N/R | N/R | N/R | N/R |
| -0319-7 | 1 | 3050 | 4283 | 0.320 | 70.57 | 141 | 26.27 | 1.63 | N/R | N/R | N/R | N/R | N/R |
| -0325-7 | 1 | 3000 | 4212 | 0.326 | 71.51 | 122.3 | 24.95 | 1.36 | 14.96 | 77.11 | 85.88 | 62.15 | 70.92 |
| -0506-7 | 2 | 3560 | 4999 | 0.549 | 67.4 | 113.1 | 22.38 | 1.35 | N/R | N/R | N/R | N/R | N/R |
| -0708-7 | 4 | 3260 | 3325 | 1.650 | 59.38 | 97.22 | 24.99 | 1.22 | N/R | N/R | N/R | N/R | N/R |
| -0908-7 | 8 | 3140 | 3202 | 3.426 | 70.73 | 102.6 | 30.39 | 1.02 | 12.3 | 96.69 | 99.86 | 84.39 | 87.56 |
| -1014-7 | 8 | 3030 | 3090 | 3.551 | 80.57 | 121 | 30.37 | 1.12 | 13 | 86.3 | 95.96 | 73.3 | 82.96 |
| Average | 1 | 3040 | 4268 | 0.321 | 74.22 | 133.5 | 26.51 | 1.44 | 16.45 | 77.71 | 87.37 | 61.26 | 70.92 |
| Std. dev. |  | 27 | 38 | 0.003 | 4.24 | 7.9 | 2.31 | 0.14 | 2.11 | 0.85 | 2.10 | 1.26 | 0.01 |
| Average | 8 | 3085 | 3146 | 3.489 | 75.65 | 111.80 | 30.38 | 1.07 | 12.65 | 91.50 | 97.91 | 78.85 | 85.26 |
| Std. dev. |  | 78 | 79 | 0.088 | 6.96 | 13.01 | 0.01 | 0.07 | 0.49 | 7.35 | 2.76 | 7.84 | 3.25 |

*Theoretical yield based on the particle size analysis

Consistent with the 100 gram scale experiments, the results in Table 3 show that the width of the distribution of the microparticle size decreases with increasing residence time of the emulsion in the series of static mixers. As shown in Table 3, the average residence time for one static mixer was 0.321 sec, resulting in a CoV$_m$ of 1.44. Increasing the average residence time to 3.489 sec through the use of eight mixers, decreased the CoV$_m$ to 1.07. The longer average residence time also increased the average yield in a desired microparticle size range of 25–125 μm by 28.71%, and in a desired microparticle size range of 25–150 μm by 20.22%.

The experiments and data described above demonstrate that the mass median diameter of the microparticles is inversely proportional to the average emulsion velocity through the static mixer. The experiments and data also demonstrate that the width of the microparticle size distribution (CoV$_m$), and its symmetry, can be controlled by the residence time of the emulsion in the static mixer, or series of static mixers. Helical design static mixers, scissors design static mixers, and layered design static mixers all appear to behave similarly with respect to changes in velocity or residence time.

Example 2

Preparation of Risperidone Microparticles Using a Manifold

Microparticles comprising risperidone were prepared at the 20-kilogram scale. The 20 Kg process (8 Kg of active agent and 12 Kg of polymer) provides a theoretical drug loading of the microparticles of 40% (8 Kg/20 Kg×100%).

The polymer solution was prepared by dissolving 12.0 Kg of MEDISORB® 7525 DL polymer (Alkermes, Inc., Blue Ash, Ohio) in 60 Kg of ethyl acetate (Merck). The polymer was added to the solvent at 25° C. in a stainless steel reactor. The temperature of the tank was raised to 37° C. to facilitate dissolution. The vessel was agitated for at least 16 hours to dissolve the polymer. Once dissolved, the solution temperature was reduced to 25° C.

The drug solution was prepared by dissolving 8.0 Kg of risperidone base (Janssen Pharmaceutica, Beerse, Belgium) in 25.3 Kg of benzyl alcohol (Merck) at 25° C. in a stainless steel reactor. The organic phase was prepared by adding the drug solution to the polymer solution at 25° C. in a stainless steel reactor and mixing for at least 15 minutes.

The continuous or aqueous phase was prepared by dissolving 6.0 Kg of polyvinyl alcohol (PVA) (DuPont) in 594.0 Kg hot (>60° C.) water for injection (WFI) in a stainless steel vessel to form a 1% solution. The vessel was agitated for at least 6 hours to dissolve the PVA. Once the PVA was dissolved, the temperature was reduced to 25° C. and 42.0 Kg of ethyl acetate (Merck) was added, and mixed for at least 30 minutes to dissolve the ethyl acetate.

Figure 7:
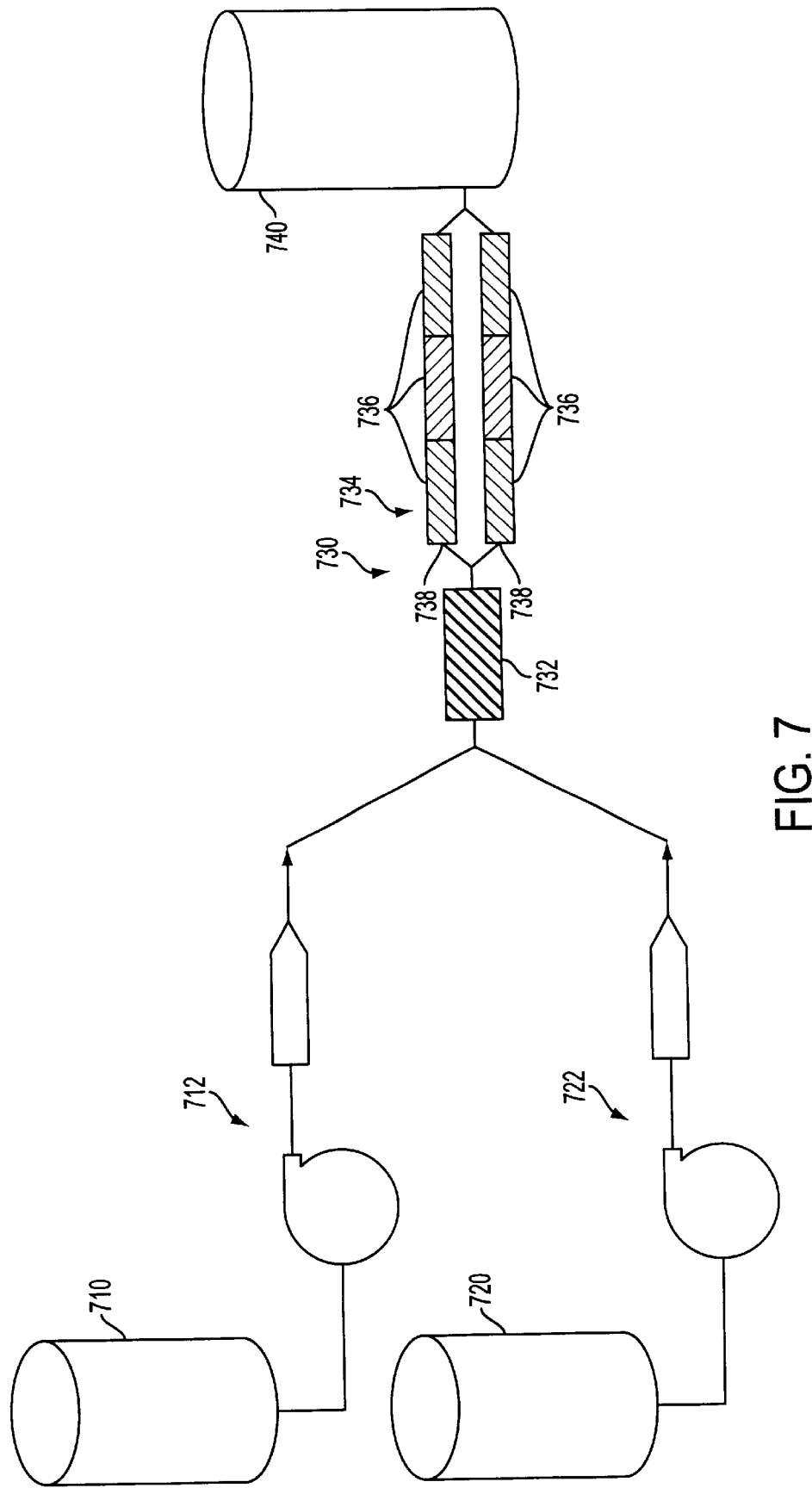
FIG. 7 shows an exemplary embodiment of an equipment configuration for preparing microparticles in accordance with the present invention.

Using positive displacement pumps, the organic and aqueous phases were pumped through a static mixing assembly to form an oil-in-water emulsion. A preferred system for carrying out this process is shown in FIG. 7. An organic phase 710 (polymer/drug solution) is pumped by a pump 712. A continuous phase 720 (PVA solution) is pumped by a pump 722. The organic and continuous phases are pumped into a static mixing assembly 730. Preferably, static mixing assembly 730 comprises a preblending static mixer 732 and a manifold 734. Manifold 734 preferably comprises a plurality of individual static mixers 736 configured to provide a plurality of parallel flow streams 738. Although FIG. 7 shows two parallel flow streams in manifold 734, the present invention is not limited to the use of two flow streams, and more or less flow streams could be used in manifold 734, as would be readily apparent to one skilled in the art. Similarly, FIG. 7 shows three individual static mixers 736 arranged in series to form flow streams 738. It should be readily apparent to one skilled in the art that other numbers, more or less, of static mixers 736 could be used to form flow streams 738.

The emulsion droplet size, and the resulting microparticle size, are controlled primarily by the flow rate and residence time through the static mixing assembly. The static mixing assembly used in the 20 Kg risperidone process consisted of a two inch diameter preblending static mixer upstream of a two flow stream manifold. Each flow stream in the manifold was formed by three, eighteen inch long, one inch diameter static mixers arranged in series. The larger diameter of the preblending static mixer is important to accommodate the total flow from the organic and aqueous phase feed streams at a lower velocity than the smaller diameter static mixers in the manifold.

The flow rates are set by nominal pump speed settings. The total flow rate was approximately 20–22 Kg/min, divided between the two flow streams in the manifold. The total flow rate can be divided one-half for each flow stream in the manifold, or in any other manner as would be readily apparent to one skilled in the art.

The flow rates for seven 20 Kg batches of microparticles are shown below in Table 4. In batches 03098, 03168, and 03238, the drug (risperidone) was not present, resulting in the production of "placebo" microparticles.

TABLE 4

20 kg Emulsion flow rate summary

| Batch | w:o ratio w/w | Rate water kg/min | Rate oil kg/min | Rate Total kg/min |
|---|---|---|---|---|
| -03098 | 4.84 | 16.8 | 3.47 | 20.3 |
| -03168 | 4.84 | 16.8 | 3.47 | 20.3 |
| -03238 | 4.86 | 16.8 | 3.47 | 20.3 |
| -03308 | 4.70 | 16.8 | 3.57 | 20.3 |
| -04068 | 4.67 | 17.0 | 3.63 | 20.6 |
| -04138 | 4.50 | 16.9 | 3.75 | 20.7 |
| -04208 | 4.46 | 16.8 | 3.78 | 20.6 |
| Average | 4.7 | 16.8 | 3.6 | 20.4 |
| SD | 0.2 | 0.1 | 0.1 | 0.2 |

After exiting the static mixing assembly, the oil-in-water emulsion is transferred to a large agitated tank for solvent extraction or quench (extraction vessel 740 in FIG. 7). The aqueous quench consisted of 4875 Kg WFI and 125 Kg ethyl acetate at 6° C. Solvents are extracted from the emulsion droplets, thereby hardening into microparticles. The microparticles were sampled from the extraction vessel and analyzed using a Coulter LQ100 particle size analyzer. The particle size results from these experiments are shown below in Table 5.

TABLE 5

Particle Size Characteristics

| Batch # | Mean (um) | Std. Dev. | % < 150 um |
|---|---|---|---|
| 0309-8 | 83.03 | 40.44 | 95.7 |
| 0316-8 | 80.14 | 43.79 | 94.5 |
| 0323-8 | 80.81 | 40.81 | 95.8 |
| 0330-8 | 82.24 | 36.9 | 97.7 |
| 0406-8 | 78.21 | 34.53 | 99 |
| 0413-8 | 80.47 | 35.31 | 98.5 |
| 0420-8 | 79.55 | 35.75 | 98.5 |
| Average | 80.64 | 38.22 | 97.10 |
| Std. Dev | 1.62 | 3.48 | 1.75 |

As can be seen from Table 5, the percentage of microparticles within the desired microparticle size range of less than 150 $\mu$m ranged from 94.5% to 99%, with an average of 97.1%. Through the use of the static mixing assembly, the particle size characteristics could be controlled to provide a desired microparticle size range.

It should be understood by one skilled in the art that the present invention is not limited to the use of an individual static mixer for any of the elements depicted as individual static mixers in the Figures. As would be readily apparent to one skilled in the art, a plurality of individual static mixers arranged in series could be used, or a manifold containing a plurality of individual static mixers arranged in series, or arranged in parallel to provide a plurality of parallel flow streams, could also be used.

Example 3

Methods for Preparing Microparticles

As exemplified by the examples discussed above, methods for preparing microparticles in accordance with the present invention will now be described in more detail. In one embodiment of the present invention, a first phase, comprising an active agent and a polymer, is prepared. In one embodiment, the first phase is prepared by dissolving the active agent in a first solvent to form an active agent solution. The polymer is dissolved in a second solvent to form a polymer solution. The active agent solution and the polymer solution are blended to form the first phase. In a particularly preferred embodiment, the active agent is selected from the group consisting of risperidone, 9-hydroxyrisperidone, and pharmaceutically acceptable salts thereof. In such an embodiment, a preferred first solvent is benzyl alcohol, and a preferred second solvent is ethyl acetate.

In another embodiment of the present invention, the first phase is prepared by dissolving the active agent and the polymer in a solvent to form a solution. In a particularly preferred embodiment, the active agent is bupivacaine, and the solvent is ethyl acetate. It should be understood that the present invention is not limited to any particular method or process by which the first phase is prepared, and other suitable processes would be readily apparent to one skilled in the art.

A second phase is prepared, and combined with the first phase in a first static mixer to form an emulsion. In a preferred embodiment, the two phases are pumped into the static mixer, with the second phase being pumped at a flow rate greater than the flow rate of the first phase. In one preferred embodiment, the ratio of the flow rate of the second phase to the flow rate of the first phase is from about 4:1 to about 5:1. However, it should be understood by one skilled in the art that the present invention is not limited to such a flow rate ratio, and other appropriate flow rate ratios would be readily apparent to one skilled in the art.

The emulsion flows through a manifold that includes a plurality of static mixers into a quench liquid whereby droplets of the emulsion form microparticles. The quench liquid is prepared in a manner well known to one skilled in the art. The quench may be water, such as WFI or it may be an aqueous solution comprising one or more solvents.

Preferably, the diameter of the first static mixer is greater than the diameter of each of the plurality of static mixers in the manifold. In one embodiment, the plurality of static mixers is configured to provide a plurality of parallel flow streams. In a particularly preferred embodiment, the plurality of static mixers in the manifold is two. However, it should be understood by one skilled in the art that the present invention is not limited to the use of two static mixers in such a configuration, and other appropriate numbers of static mixers would be readily apparent to one skilled in the art. Alternatively, the plurality of static mixers can be configured in series to provide a plurality of sequential flow streams.

The step of flowing the emulsion through the manifold is preferably performed by flowing a portion of a total flow rate through each of the static mixers in the manifold, the total flow rate being the sum of the flow rate of the first phase and the flow rate of the second phase. For example, for a manifold configured with two static mixers, a portion of the total flow rate will flow through each of the two static mixers. The portion flowing through each of the two static mixers can be one-half, or other portions as would be readily apparent to one skilled in the art.

An alternate method for preparing microparticles in accordance with the present invention will now be described. A first phase, comprising an active agent and a polymer, is prepared. A second phase is prepared, and combined with the first phase in a first static mixer to form an emulsion, the emulsion forming an outflow of the first static mixer. Suitable methods and processes for preparing the first and second phases, and for combining in the first static mixer, have been described above and will not be repeated here for brevity.

The outflow of the first static mixer is divided to form at least two flow streams. Each of the at least two flow streams flows through a separate second static mixer. The separate second static mixer can be an individual static mixer, one of a plurality of individual static mixers arranged in series, or one of a plurality of individual static mixers configured to provide a plurality of parallel flow streams. Preferably, the diameter of the first static mixer is greater than the diameter of each separate second static mixer. The at least two flow streams may have substantially equal flow rates, or such other flow rates as would be apparent to one skilled in the art.

The at least two flow streams are combined with a quench liquid whereby droplets of the emulsion form microparticles. The quench liquid can be the same as, or different from, the second phase.

A method for controlling particle size distribution of microparticles in accordance with the present invention will now be described. In a manner as described above, a first phase, comprising an active agent and a polymer, is prepared. A second phase is prepared, and combined with the first phase in a static mixing assembly to form an emulsion. The emulsion flows into a quench liquid whereby droplets of the emulsion form microparticles. The residence time of the emulsion in the static mixing assembly is adjusted to obtain a predetermined particle size distribution of the resulting microparticles. The residence time is equal to a length of the static mixing assembly divided by an average velocity of the emulsion through the static mixing assembly. Increasing the residence time of the emulsion in the static mixing assembly narrows the particle size distribution. Similarly, decreasing the residence time of the emulsion in the static mixing assembly broadens the particle size distribution. The residence time may be adjusted by changing the length of the static mixing assembly. In one embodiment, the residence time is from about three seconds to about four seconds. However, it should be understood by one skilled in the art that the present invention is not limited to such a residence time, and other residence times may be used.

In one embodiment of the present invention, the static mixing assembly comprises a plurality of individual static mixers configured so that the emulsion flows sequentially through the plurality of individual static mixers. In an alternate embodiment, the static mixing assembly comprises a first static mixer and a manifold, in fluid communication with the first static mixer, which includes a plurality of static mixers. In such an alternate embodiment, the diameter of the first static mixer is preferably greater than the diameter of each of the plurality of static mixers in the manifold.

Microparticles of the Present Invention

The microparticles prepared by the process of the present invention preferably comprise a polymeric binder, but it should be understood by one skilled in the art that the present invention is not limited to preparation of microparticles comprising a polymeric binder. Suitable polymeric binder materials include poly(glycolic acid), poly-d,1-lactic acid, poly-1-lactic acid, copolymers of the foregoing, poly (aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, albumin, casein, and waxes. Poly (d,1-lactic-co-glycolic acid) is commercially available from Alkermes, Inc. (Blue Ash, Ohio). A suitable product commercially available from Alkermes, Inc. is a 50:50 poly(d,1-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,1-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,1-PLA (Resomer® RG 206), and from Birmingham Polymers (Birmingham, Ala.). These copolymers are available in a wide range of molecular weights and ratios of lactic acid to glycolic acid.

One type of microparticle suitable for preparation by the present invention is a sustained-release microparticle that is biodegradable. However, it should be understood by one skilled in the art that the present invention is not limited to biodegradable or other types of sustained-release microparticles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is useful in according multiphasic release patterns.

The microparticles prepared in accordance with the present invention may include an active agent or other type of substance that is released from the microparticles into the host. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl]ethyl]-6,7,8,9-tetrahydro-2-methyl-4H--pyrido[1,2-a]pyrimidin-4-one ("risperidone") and 3-[2-[4-(6-fluoro-1,2-benzisoxazol-3-yl)-1-piperidinyl]ethyl]-6,7,8,9-tetrahydro-9-hydroxy-2-methyl-4H--pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; major tranquilizers such as chlorpromazine HCl, clozapine, mesoridazine, metiapine, reserpine, thioridazine and the like; minor tranquilizers such as chlordiazepoxide, diazepam meprobamate, temazepam and the like; rhinological decongestants; sedative-hypnotics such as codeine, phenobarbital, sodium pentobarbital, sodium secobarbital and the like; steroids such as testosterone and tesosterone propionate; sulfonamides; sympathomimetic agents; vaccines; vitamins and nutrients such as the essential amino acids; essential fats and the like; antimalarials such 4-aminoquinolines, 8-aminoquinolines, pyrimethamine and the like, anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocornine methanesulfonate, dihydroergokroyptine methanesulfate and combinations thereof; alkaloids such as atropine sulfate, Belladonna, hyoscine hydrobromide and the like; analgetics, narcotics such as codeine, dihydrocodienone, meperidine, morphine and the like; non-narcotics such as salicylates, aspirin, acetaminophen, d-propoxyphene and the like; antibiotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracylines, and the like, anti-cancer agents; anti-convulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa; chlorambucil, cyclophosphamide, melphalan, nitrogen mustard, methotrexate and the like; antigens of such microorganisms as *Neisseria gonorrhea, Mycobacterium tuberculosis,* Herpes virus (homonis, types 1 and 2), *Candida albicans, Candida tropicalis, Trichomonas vaginalis, Haemophilus vaginalis,* Group B *Streptococcus ecoli, Mycoplasma hominis, Haemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobacillus seminis, Mycoplasma bovigenitalium, Aspergillus fumigatus, Absidia ramosa, Trypanosoma equiperdum, Babesia caballi, Clostridium tetani,* and the like; antibodies that counteract the above microorganisms; and enzymes such as ribonuclease, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, and DPN-di-aprorasse.

Other suitable active agents include estrogens such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengestrol, norethynodrel and the like; and the spermicidal compounds such as nonylphenoxypolyoxyethylene glycol, benzethonium chloride, chlorindanol and the like.

Still other suitable active agents include antifungals, antivirals, anticoagulants, anticonvulsants, antidepressants, antihistamines, hormones, vitamins and minerals, cardiovascular agents, peptides and proteins, nucleic acids, immunological agents, antigens of such bacterial organisms as *Streptococcus pneumoniae, Haemophilus influenzae, Staphylococcus aureus, Streptococcus pyogenes, Corynebacterium diphtheriae, Bacillus anthracis, Clostridium tetani, Clostridium botulinum, Clostridium perfringens, Streptococcus mutans, Salmonella typhi, Haemophilus parainfluenzae, Bordetella pertussis, Francisella tularensis, Yersinia pestis, Vibrio cholerae, Legionella pneumophila, Mycobacterium leprae, Leptospira interrogans, Borrelia burgdorferi, Campylobacter jejuni,* antigens of such viruses as smallpox, influenza A and B, respiratory syncytial, parainfluenza, measles, HIV, varicella-zoster, herpes simplex 1 and 2, cytomegalovirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, antigens of such fungal protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydia psittaci, Chlamydia trachomatis, Plasmodium falciparum, Trypanosoma brucei, Entamoeba histolytica, Toxoplasma gondii, Trichomonas vaginalis, Schistosoma mansoni.* These antigens may be in the form of whole killed organisms, peptides, proteins, glycoproteins, carbohydrates, or combinations thereof.

Still other macromolecular bioactive agents that may be chosen for incorporation include, but are not limited to, blood clotting factors, hemopoietic factors, cytokines, interleukins, colony stimulating factors, growth factors, and analogs and fragments thereof.

The microparticles can be mixed by size or by type. However, it should be understood that the present invention is not limited to the use of biodegradable or other types of microparticies that contain an active agent. In one embodiment, the microparticles are mixed in a manner that provides for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

CONCLUSION

While various embodiments of the present invention have been described above, it should be understood that they have been presented by way of example only, and not limitation. The present invention is not limited to the preparation of controlled release microparticles, nor is it limited to a particular active agent, polymer or solvent, nor is the present invention limited to a particular scale or batch size. The present invention is not limited to any type or design of static mixer. Thus, the breadth and scope of the present invention should not be limited by any of the above-described exemplary embodiments, but should be defined only in accordance with the following claims and their equivalents.

What is claimed is:

1. A method of preparing microparticles, comprising:
   preparing a first phase, the first phase comprising an active agent and a polymer;
   preparing a second phase;
   preparing a quench liquid;
   pumping the first phase and the second phase through a first static mixer to form an emulsion; and
   flowing the emulsion through a manifold that includes a plurality of static mixers into the quench liquid whereby droplets of the emulsion form microparticles.

2. The method of claim 1, wherein a diameter of the first static mixer is greater than a diameter of each of the plurality of static mixers in the manifold.

3. The method of claim 1, wherein the pumping step is performed wherein the first phase is pumped at a first flow rate and the second phase is pumped at a second flow rate greater than the first flow rate.

4. The method of claim 3, wherein a ratio of the second flow rate to the first flow rate is from about 4:1 to about 5:1.

5. The method of claim 3, wherein the flowing step is performed by flowing a portion of a total flow rate through each of the plurality of static mixers in the manifold, wherein the total flow rate is the sum of the first flow rate and the second flow rate.

6. The method of claim 5, wherein the plurality of static mixers in the manifold is two.

7. The method of claim 1, wherein the first static mixer comprises a plurality of static mixing elements received within a conduit.

8. The method of claim 7, wherein each of the plurality of static mixers in the manifold comprises a plurality of static mixing elements received within a conduit.

9. The method of claim 1, wherein the step of preparing the first phase comprises:
   dissolving the active agent in a first solvent to form an active agent solution;
   dissolving the polymer in a second solvent to form a polymer solution; and
   blending the active agent solution and the polymer solution.

10. The method of claim 9, wherein the active agent is selected from the group consisting of risperidone, 9-hydroxyrisperidone, and pharmaceutically acceptable salts thereof.

11. The method of claim 10, wherein the first solvent is benzyl alcohol.

12. The method of claim 10, wherein the polymer is poly(d,l-lactide-co-glycolide) having a molar ratio of lactide to glycolide in the range of from about 85:15 to about 50:50.

13. The method of claim 12, wherein the second solvent is ethyl acetate.

14. A method of preparing microparticles, comprising:
   preparing a first phase, the first phase comprising an active agent and a polymer;
   preparing a second phase;
   preparing a quench liquid;
   combining the first phase and the second phase in a first static mixer to form an emulsion, the emulsion forming an outflow of the first static mixer;
   dividing the outflow of the first static mixer to form at least two flow streams;
   flowing each of the at least two flow streams through a separate second static mixer; and
   combining the at least two flow streams with the quench liquid whereby droplets of the emulsion form microparticles.

15. The method of claim 14, wherein a diameter of the first static mixer is greater than a diameter of each separate second static mixer.

16. The method of claim 14, wherein the step of preparing the first phase comprises:
   dissolving the active agent in a first solvent to form an active agent solution;
   dissolving the polymer in a second solvent to form a polymer solution; and
   blending the active agent solution and the polymer solution.

17. The method of claim 16, wherein the active agent is selected from the group consisting of risperidone, 9-hydroxyrisperidone, and pharmaceutically acceptable salts thereof.

18. The method of claim 17, wherein the first solvent is benzyl alcohol.

19. The method of claim 16, wherein the polymer is poly(d,l-lactide-co-glycolide) having a molar ratio of lactide to glycolide in the range of from about 85:15 to about 50:50.

20. The method of claim 19, wherein the second solvent is ethyl acetate.

21. The method of claim 14, wherein the at least two flow streams have substantially equal flow rates.

22. A microencapsulated active agent prepared by a method for preparing microparticles, the method comprising:
   preparing a first phase, the first phase comprising an active agent and a polymer;
   preparing a second phase;
   preparing a quench liquid;
   pumping the first phase and the second phase through a first static mixer to form an emulsion; and
   flowing the emulsion through a manifold that includes a plurality of static mixers into the quench liquid whereby droplets of the emulsion form microparticles.

23. A microencapsulated active agent prepared by a method for preparing microparticles, the method comprising:
   preparing a first phase, the first phase comprising an active agent and a polymer;
   preparing a second phase;
   preparing a quench liquid;
   combining the first phase and the second phase in a first static mixer to form an emulsion, the emulsion forming an outflow of the first static mixer;
   dividing the outflow of the first static mixer to form at least two substantially identical flow streams;
   flowing each of the at least two substantially identical flow streams through a separate second static mixer; and
   combining the least two substantially identical flow streams with the quench liquid whereby droplets of the emulsion form microparticles.

24. A system for preparing microparticles, comprising:

a first pump;

a second pump;

a first static mixer in fluid communication with said first pump and with said second pump, wherein said first pump is configured to pump an organic phase into said first static mixer, and said second pump is configured to pump a continuous phase into said first static mixer;

a manifold in fluid communication with said first static mixer, said manifold comprising a plurality of static mixers; and an extraction vessel in fluid communication with said manifold, wherein an outflow of said first static mixer flows through said manifold into said extraction vessel.

25. The system of claim 24, wherein said first pump is configured to operate at a first flow rate, and said second pump is configured to operate at a second flow rate greater than said first flow rate.

26. The system of claim 25, wherein a ratio of said second flow rate to said first flow rate is from about 4:1 to about 5:1.

27. The system of claim 24, wherein a diameter of said first static mixer is greater than a diameter of each of said plurality of static mixers in said manifold.

28. The system of claim 24, wherein said plurality of static mixers in said manifold is two.

29. The system of claim 27, wherein said plurality of static mixers in said manifold is two.

30. The system of claim 24, further comprising:

a first vessel in fluid communication with said first pump; and a second vessel in fluid communication with said second pump.

31. A method for controlling particle size distribution of microparticles, comprising:

preparing a first phase, the first phase comprising an active agent and a polymer;

preparing a second phase;

preparing a quench liquid;

pumping the first phase and the second phase through a static mixing assembly to form an emulsion;

flowing the emulsion into the quench liquid whereby droplets of the emulsion form microparticles; and adjusting a residence time of the emulsion in the static mixing assembly to obtain a predetermined particle size distribution of the resulting microparticles, wherein the residence time is equal to a length of the static mixing assembly divided by an average velocity of the emulsion through the static mixing assembly.

32. The method of claim 31, wherein the adjusting step is carried out to increase the residence time, thereby narrowing particle size distribution.

33. The method of claim 31, wherein the adjusting step is carried out to decrease the residence time, thereby broadening particle size distribution.

34. The method of claim 31, wherein the static mixing assembly comprises a plurality of individual static mixers configured so that the emulsion flows sequentially through the plurality of individual static mixers.

35. The method of claim 31, wherein the static mixing assembly comprises:

a first static mixer; and a manifold that includes a plurality of static mixers, the manifold in fluid communication with the first static mixer.

36. The method of claim 35, wherein a diameter of the first static mixer is greater than a diameter of each of the plurality of static mixers in the manifold.

37. The method of claim 31, wherein the residence time is from about three seconds to about four seconds.

38. The method of claim 35, wherein the residence time is from about three seconds to about four seconds.

39. The method of claim 31, wherein the adjusting step is carried out by changing the length of the static mixing assembly.

40. The method of claim 6, wherein the portion of the total flow rate flowing through each of the two static mixers is one-half.

41. The method of claim 35, wherein the plurality of static mixers in the manifold are configured to provide a plurality of parallel flow streams.

42. The method of claim 36, wherein the plurality of static mixers in the manifold are configured to provide a plurality of parallel flow streams.

43. The system of claim 24, wherein said plurality of static mixers are configured in parallel.

44. The system of claim 24, wherein said plurality of static mixers are configured in series.

* * * * *